Figure 1:
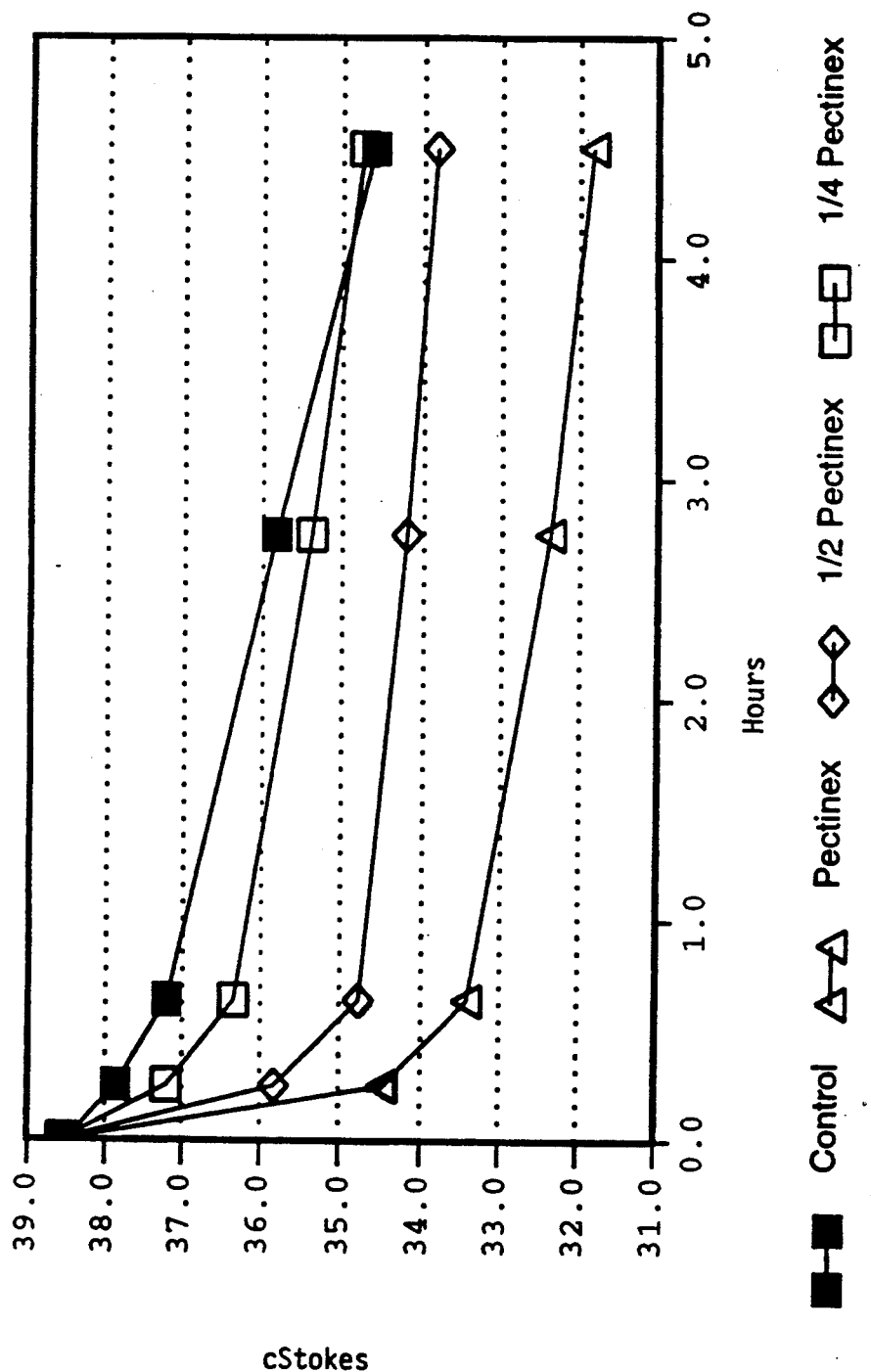

United States Patent [19]

Hernandez-Mena et al.

[11] Patent Number: 5,238,572
[45] Date of Patent: Aug. 24, 1993

[54] ENZYME TREATMENT FOR INDUSTRIAL SLIME CONTROL

[75] Inventors: Roy Hernandez-Mena, The Woodlands; Patric L. Friend, Conroe, both of Tex.

[73] Assignee: Betz Laboratories, Inc., Trevose, Pa.

[21] Appl. No.: 7,944

[22] Filed: Jan. 25, 1993

[51] Int. Cl.$^5$ .............................................. C02F 1/50
[52] U.S. Cl. .................................. 210/632; 210/764; 162/161
[58] Field of Search ...................... 210/606, 632, 764; 162/161

[56] References Cited

U.S. PATENT DOCUMENTS

| | | | |
|---|---|---|---|
| 3,773,623 | 11/1973 | Hatcher et al. | 210/632 |
| 3,824,184 | 7/1974 | Hatcher et al. | 210/1 |
| 4,055,467 | 10/1977 | Christensen et al. | 162/161 |
| 4,293,559 | 10/1981 | Buckman et al. | 162/161 |
| 4,370,199 | 1/1983 | Orndorff | 210/632 |
| 4,684,469 | 8/1987 | Pedersen et al. | 210/632 |
| 4,936,994 | 6/1990 | Wiatr | 210/632 |
| 4,966,716 | 10/1990 | Favstritsky et al. | 210/764 |
| 5,071,765 | 12/1991 | Wiatr | 435/264 |

FOREIGN PATENT DOCUMENTS 1274442 9/1990 Canada.

OTHER PUBLICATIONS

Nelson et al., Decomposition of Exopolysaccharide Slime By A Bacteriophage Enzyme, 1988, pp. 1185-1188.

Sutherland, Phage-Induced Fucosidases Hydrolysing the Exopolysaccharide of Klebsiella aerogenes Type 54, 1967, pp. 278-285.

Primary Examiner—Thomas Wyse
Attorney, Agent, or Firm—Alexander D. Ricci; Gregory M. Hill

[57] ABSTRACT

A method for treating the microbial slime that is generated in industrial water systems by adding to the water a combination of enzymes specific to the numerous saccharide units that make up the exopolysaccharide layer. These enzymes comprise galactosidase, galacturonidase, rhamnosidase, xylosidase, fucosidase, arabinosidase and α-glucosidase.

4 Claims, 1 Drawing Sheet

ENZYME TREATMENT FOR INDUSTRIAL SLIME CONTROL

FIELD OF THE INVENTION

The present invention relates to the treatment of slime deposits produced by microbes in industrial aqueous systems. This method of treating slime is specifically directed toward papermaking and cooling water systems.

BACKGROUND OF THE INVENTION

Microorganisms and the slimes they produce are responsible for the formation of deposits in papermaking and industrial cooling water systems. Bacterial slimes are composed of exopolysaccharides (EPS) which exist as capsules or slime layers outside of the cell walls. When these slimes form on surfaces in paper or cooling systems, they trap organic and inorganic components and debris present in the process waters. As the microorganisms grow within paper system deposits, portions of the deposit may detach from the surface and cause paper breaks and spots in produced paper, which reduces the paper quality and increases machine downtime. Microbial growth and slime formation in cooling systems results in reduced heat exchange caused by biofouling and plugging of heat exchanger tubes, excessive fouling of the cooling water, tower decks and fill, and is a potential cause of under-deposit corrosion.

The term "slime" is a broad one covering a wide range of viscous, mucous, or leathery materials and mixtures found in industrial waters. Slimes are polymeric in nature and can be broadly classified as chemical, biological, or composite slimes depending upon their cause or composition. For example, raw materials and equipment used in the paper industry are not sterile and water used in conjunction with such equipment is continuously being contaminated with a wide variety of micro organisms from such sources as wood pulp, chemicals, air, makeup water, and the like. The growth of certain specific forms of these biological contaminants causes or produces polymeric excretions or products that are or become slime.

Historically, slime formation has been treated by the addition to industrial waters (e.g., white water associated with the pulp and paper industry) of slimicides. The purpose of these slimicides is to destroy or arrest the growth of some of the many organisms present in the water to thereby prevent or retard the formation of slime. Chemicals used as slimicides have included chlorine, phenylmercuric acetate, pentachlorophenol, tributyl tin oxide, and isothiocyanates, all of which are relatively toxic to humans.

Microbially produced exopolysaccharides can build up, retard heat transfer and restrict water flow through cooling water systems. Controlling slime-forming bacteria by applying toxic chemicals is becoming increasingly unaccepted due to environmental problems. In addition, the efficacy of the toxicants is minimized by the slime itself, since the extracellular polysaccharide surrounding microorganisms impedes toxicant penetration.

Toxicants cannot adequately control large populations of attached bacteria and they are effective mainly against floating microorganisms. Although surfactants and dispersants which penetrate and help loosen slime can enhance the activity of toxicants, they are nonspecific and may have deleterious effects on the industrial process or the environment.

Recently, methods directed at controlling microbial slimes include the use of enzymes. These approaches attempt to disrupt the attachment process so that slime formation is prevented, or by hydrolyzing the exopolysaccharide (EPS) produced by the microorganisms after attachment. Using an enzyme to control slime will require knowledge of the composition of the slime, so that an appropriate enzyme-substrate combination is employed.

Differing views of the composition of industrial slime deposits exist, but no data directly supporting those views have been published. Research by H. J. Hatcher (Biochemical Substances as Aids in Process Control, TPPI 62(4):93, 1980) suggests that slimes are composed of levan, a homopolysaccharide composed of repeating units of fructose. This is inconsistent with literature related to the biosynthesis of Tevans, which shows that levans can only be produced by bacteria growing on sucrose (Stanier, R. Y. E. A. Aelber, and J. L. Ingraham; Structure and Function in Procaryotic Cells, Capsules and Slime Layers, *The Microbial World.* pp. 335-337, Prentice-Hall, Inc., Englewood Cliffs, N.J., 1975). During levan biosynthesis, the fructose unit of sucrose is incorporated into levan, while the glucose unit is used for energy and growth by the microorganism. It is unlikely that bacteria in paper or cooling systems will encounter sucrose in significant amounts, and hence levans should not be a significant component of industrial slimes.

A recent Canadian Patent, No. 1,274,442, suggested that EPS of industrial water systems may be composed of alginate, a polysaccharide composed of mannuronic and guluronic acids. U.S. Pat. No. 4,936,994, claimed that microbial slime in industrial systems can be controlled using cellulase, α-amylase, and protease, which presupposes that the slimes result from polymers of α-and β-linked glucose residues and protein.

These differing views can be contrasted with those more commonly accepted in the technical literature, that slime-producing bacteria form heteropolysaccharides consisting of monosaccharides such as glucose, mannose, galactose, and glucuronic acid. Studies have shown that the composition of EPS is usually independent of the substrate or carbon source used for growth and polysaccharide production (Sutherland, I. W. Bacterial Exopolysaccharides-Their nature and Production, *Surface Carbohydrates of the Procaryotic Cell* (Sutherland, I. W., ed), pp, 27-96, Academic Press Inc. Ltd., London, 1977). It was therefore felt that slimes found in industrial cooling and papermaking systems were likely to be composed of mixed heteropolysaccharides.

It is an object of the present invention to provide a microbial slime treatment program which will more effectively break down or altogether prevent the production of microbial exopolysaccharide slime than any of the other treatment approaches heretofore employed. This is achieved by using a combination of enzymes that are specific to each of the saccharides present in the slime layer.

DESCRIPTION OF THE INVENTION

The present invention comprises adding to aqueous systems experiencing microbial slime problems a combination of enzymes each specific to the numerous sugars and linkages present in the exopolysaccharide slime biomass. These enzymes are galactosidase, galacturonidase, rhamnosidase, xylosidase, fucosidase, arabinosidase and α-glucosidase. An effective treatment should include all of these enzymes. However, certain exopolysaccharide layers may be treated with fewer than all of these with the proviso that rhamnosidase and fucosidase are always present.

These enzymes may be blended as desired by the user or they may be procured from various commercial sources as pre-blended combinations. Examples include Novozym 234 (Novo Bio Labs), Spark-L (Miles) and SP-249 (Novo/Nordisk).

The amount of enzyme treatment according to the present invention will vary depending upon the severity of the microbially produced slime problem. Nonetheless, for example, if using Novozym 234, from 20 to 200 ppm of the enzyme blend is generally sufficient.

The enzyme treatment of the present invention is to be employed in aqueous systems where microbial slime causes problems. Systems which are particularly susceptible to slime proliferation are papermaking and cooling water systems. The present enzyme treatment is especially effective in these applications.

The types of slime producing bacteria present in these water systems may vary. However, the most predominant microbes found are Pseudomonas, Klebsiella, Aerobacter, Acinetobacter, Enterobacter and Flavobacterium. Although the exopolysaccharide layer produced by each of these bacteria might differ somewhat, it has been found that the saccharides present are glucose, mannose, galactose, rhamnose, fucose and glucuronic acid.

Slime deposits from 16 sites located throughout the U.S. were extracted and analyzed. Results of this analysis are shown in Table I.

TABLE I

Summary of Carbohydrate Compositions for Biological Field Samples

| SOURCE | COMPOSITION |
| --- | --- |
| Cooling Tower, LA | fucose, mannose, glucose, glucuronic acid |
| Paper Mill, Washington | fucose, galactose, glucose, glucuronic acid |
| Paper Mill, PA | rhamnose, galactose, mannose, glucose |
| Paper Mill Saveall, PA | rhamnose, galactose, mannose, glucose |
| Paper Mill AES, PA | rhamnose, fucose, galactose, mannose, glucose |
| Cooling Tower, Georgia | rhamnose fucose, galactose, mannose, glucose, glucuronic acid |
| Paper Mill, Georgia | rhamnose, fucose, galactose, mannose, glucose, glucuronic acid |
| Paper Mill, Georgia | rhamnose, fucose, galactose, mannose, glucose |
| Paper Mill, California | rhamnose, fucose, galactose, mannose, glucose, glucuronic acid |
| Sulfur Bacteria, Well, FL | rhamnose, fucose, galactose, mannose, glucose, glucuronic acid |
| Refinery Cooling Tower, TX | rhamnose, fucose, galactose, mannose, glucose |
| Cooling Tower, LA | rhamnose, fucose, galactose, mannose, glucose |
| Refinery Cooling Tower, LA | rhamnose fucose, galactose, mannose, glucose |
| Cooling Tower, LA | rhamnose, fucose, galactose, mannose, glucose, glucuronic acid |

EXAMPLE 1

In order to show the efficacy of the enzyme treatment of the present invention, an assay technique was devised based on measuring the viscosities of a slime containing solution before and after various enzyme treatments. It is generally accepted that reductions in the chain length of the polysaccharides (caused by the enzyme breaking the polymeric chain) will result in a measurable drop in solution viscosity.

Exopolysaccharides were obtained from two organisms typically found in cooling and papermaking systems. These organisms produced excessive amounts of slime which was easily isolated in pure form. Several enzymes and enzyme preparations were tested against model polysaccharides.

Assay Procedure

Viscometer: Ubbelohde micro-viscometer (Schott-Gerate).

Sample volume:
3 ml of 2 mg/ml Klebsiella (ATCC 8308) polysaccharide solution or
3 ml of 1.5 mg/ml Pseudomonas (ATCC 31260) polysaccharide solution.

Enzyme volume: 50 microliters per sample.
Assay Temperature: 37° C.

Be measuring the time required for the meniscus of the treated sample to traverse between two reference points, monitored over 24 hours, and comparing that data to a control with no enzyme treatment, a drop in viscosity over time by use of that enzyme treatment is shown.

TABLE II

| | Percent Reduction in Viscosity | |
| --- | --- | --- |
| Enzyme Used | Percent Reduction Klebsiella | Percent Reduction Pseudomonas |
| Novozym 234 | 14.20% | 24.10% |
| α-glucosidase | 8.52 | not run |
| Spark-L$^R$ | 7.99 | 0.81 |
| SP-249 | 0.17 | 24.53 |

Legend:
Novozym 234: (Nova Biolabs) multiple enzymes to attack α-1,3 linkages
α-glucosidase: (Sigma Chemical Co.)
Spark-L$^R$: (Miles) pectinase (specific to galacturonic acid, rhamnose, xylose, fucose, arabinose and galactose)
SP-249: (Novo Nordisk) galacturonidase, rhamnosidase, xylosidase, fucosidase, arabinosidase, galactosidase.

The above data indicate that these enzymes are breaking bonds within the polysaccharide chains.

EXAMPLE 2

*Klebsiella pneumoniae*, IPC 500 (Institute of Paper Chemistry), and *Pseudomonas aeruginosa*, ATTC 10145, were allowed to grow and attach to stainless steel test surfaces in 1500 ml of test medium containing Novozym 234 at concentrations between 2 and 200 ppm. A test unit to which was added 200 ppm of heat-treated (121° C., 15 min) Novozym 234 was included in order to confirm that enzymatic activity was responsible for any bacterial slime control observed in enzyme-treated test units. After 24 and 48 hours, 350 mL of test medium was removed and replaced with 350 ml of fresh test medium. Novozym 234 concentrations between 2 and 200 ppm were replenished at 24 and 48 hours to the appropriate test unit. Heat-treated Novozym 234 was also added to the appropriate test unit. At 72 and 144 hrs, stainless steel test surfaces were removed from each test unit and prepared for scanning electron microscopic (SEM) analysis. Each test surface was examined by SEM and photographed.

After 72 hours the test surface from the unit which had no enzyme treatment had evidence of bacterial attachment as did the test surface treated with 2 ppm of Novozym 234. At 20 and 200 ppm of Novozym 234, no bacterial attachment was observed on the test surfaces. Evidence that enzymatic activity attributed to Novozym 234 was responsible in the disruption of bacterial attachment was confirmed by bacterial attachment in the presence of heat-treated Novozym 234.

Table III contains data related to the total bacterial counts (TBC) found in the bulk water of the test unit throughout the experiment. As shown, these counts remained between $10^5$ and $10^7$ CFU/mL throughout the experiment. This shows that the enzyme was not preventing attachment as a result of biocidal activity. The enzyme does not function as a biocide.

TABLE III

| | Total Bacterial Counts (CFU/mL) in Bulk Water of Each Test Unit | | | | |
|---|---|---|---|---|---|
| Elapsed Time of Experiment (Hrs.) | Unit 1 Control | Unit 2 2 ppm Enzyme | Unit 3 20 ppm Enzyme | Unit 4 200 ppm Enzyme | Unit 5 200 ppm Heat-Treated Enzyme |
| 24 | $58 \times 10^7$ | $45 \times 10^7$ | $71 \times 10^7$ | $29 \times 10^7$ | $24 \times 10^7$ |
| 48 | $96 \times 10^7$ | $82 \times 10^7$ | $119 \times 10^7$ | $103 \times 10^7$ | $23 \times 10^7$ |
| 72 | $69 \times 10^7$ | $4 \times 10^5$ | $<1 \times 10^5$ | $80 \times 10^7$ | $49 \times 10^7$ |
| 144 | $54 \times 10^7$ | $84 \times 10^7$ | $6 \times 10^5$ | $195 \times 10^7$ | $180 \times 10^7$ |

This example shows that enzyme activity against polysaccharides that contain 1,3-α-linkages, controls bacterial attachment and eventual slime formation. Specifically, Novozym 234 contains 1,3-α-glucanase, 1,3-β-glucanase, laminarinase, xylanase, and chitinase enzyme activities. In studies using various para-nitrophenyl (PNP) glucosides, Novozym 234 also contains α-galactosidase which is an enzyme activity which is required for the hydrolysis of slime heteropolysaccharides.

EXAMPLE 3

Using the same test system as in Example 1 the effect of dilution of an enzyme on the rate of polysaccharide hydrolysis was examined.

Assay Procedure

Viscometer: Ubbelohde micro-viscometer (Schott Gerate).

Sample volume: 3 mL of 6.24 mg/mL Klebsiella pneumoniae exopolysaccharide solution.

Enzyme volume: 50 uliters.

Assay Temperature: 35° C.

The enzyme tested here was a pectinase enzyme, Pectinex TM, supplied by Novo/Nordisk. The enzyme was diluted to concentrations which were ¼ and ½ the original concentration. FIG. 1 is a graphical representation of the results obtained. As shown, initial hydrolysis is a function of the enzyme concentration with most activity occurring within the first hour of the experiment. This pectinase enzyme which contains enzyme activities such as pectintranseliminase, polygalacturonzase, pectinesterase, and hemicellulase is capable of hydrolyzing an exopolysaccharide involved in the adhesion of a microbe to surfaces. In studies using PNP glycosides, it was further shown that Pectinex TM contains (α-thamnosidasae and α-galactosidase activity.

Having thus disclosed our invention, what we claim is:

1. A method for treating a microbial exopolysaccharide layer on the surface of the equipment in an industrial water system comprising contacting the microbial exopolysaccharide layer with a sufficient amount for the purpose of a combination of enzymes comprised of galactosidase, galacturonidase, rhamnosidase, xylosidase, fucosidase, arabinosidase and α-glucosidase.

2. The method of claim 1 wherein from about 20 to 200 ppm of the combination of enzymes is added to the water system.

3. The method of claim 1 wherein the industrial water system is a cooling water system.

4. The method of claim 1 wherein the industrial water system is a papermaking system.

* * * * *